(12) United States Patent
von Wolff et al.

(10) Patent No.: US 10,173,993 B2
(45) Date of Patent: Jan. 8, 2019

(54) PROCESS FOR THE SYNTHESIS OF SULFONES AND SULFONAMIDES

(71) Applicant: Commissariat a l'Energie Atomique et aux Energies Alternatives, Paris (FR)

(72) Inventors: Niklas von Wolff, Paris (FR); Joëlle Char, Paris (FR); Thibault Cantat, Issy les Moulineaux (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/372,778

(22) Filed: Dec. 8, 2016

(65) Prior Publication Data

US 2017/0166542 A1   Jun. 15, 2017

(30) Foreign Application Priority Data

Dec. 9, 2015 (EP) .................................. 15306966

(51) Int. Cl.
| | | |
|---|---|---|
| *C07C 315/04* | (2006.01) | |
| *C07D 213/71* | (2006.01) | |
| *C07D 265/30* | (2006.01) | |
| *C07D 295/26* | (2006.01) | |

(52) U.S. Cl.
CPC .......... *C07D 295/26* (2013.01); *C07C 315/04* (2013.01); *C07D 213/71* (2013.01); *C07D 265/30* (2013.01)

(58) Field of Classification Search
CPC .... C07C 315/04; C07D 213/71; C07D 265/30
USPC ............................................ 564/80; 562/125
See application file for complete search history.

(56) References Cited

PUBLICATIONS

European Search Report issued in corresponding European Patent Application No. 15306966 dated May 9, 2016.
Johnson et al., "Application of Fundamental Organometallic Chemistry to the Development of a Gold-Catalyzed Synthesis of Sulfinate Derivatives," Angewandte Chemie International Edition, 53: 4404-4407 (2014).
Wang et al., "A Copper-Catalyzed Three-Component Reaction of Triethoxysilanes, Sulfur Dioxide, and Hydrazines," Organic Letters, 16: 4056-4058 (2014).

*Primary Examiner* — Venkataraman Balasubramanian
(74) *Attorney, Agent, or Firm* — Morgan, Lewis & Bockius LLP (57) ABSTRACT

A one pot single step process is described for the synthesis of a compound, including a labeled compound, containing a sulfonyl functional group comprising the step of mixing together a silane, an $SO_2$ source, an electrophilic compound, an activating compound and optionally a metal catalyst. A process for producing tracers from a labeled sulfonyl containing compound prepared by the described process is also included.

16 Claims, 4 Drawing Sheets

Figure 1

Figure 2 stoechiometric transition metal catalyzed

Figure 3 stoechiometric transition metal catalyzed

Figure 4

A = an activating compound
Nu-FG = R-Si(X)3
Electrophile = R'Y
SO₂ = SO₂ gas, a SO₂ surrogate, or a SO₂-amine adduct

Figure 5

PROCESS FOR THE SYNTHESIS OF SULFONES AND SULFONAMIDES

The present invention relates to a one pot single step process for the synthesis of a compound containing a sulfonyl functional group, in particular a sulfone or a sulfonamide, comprising the step of mixing together a silane, an $SO_2$ source, an electrophilic compound, an activating compound and optionally a metal catalyst. Labeled compounds containing a sulfonyl functional group, in particular labeled sulfones or sulfonamides can also be synthesized by the process of the invention.

The present invention also concerns the use of unlabeled or labeled sulfonyl containing compounds, in particular labeled or unlabeled sulfones and sulfonamides, obtained by a process according to the invention in the manufacture of vitamins, pharmaceuticals, adhesives, acrylic fibers and synthetic leathers, pesticides, and fertilizers, for example.

The present invention further relates to a process for producing tracers and tracers comprising a step of synthesis of a labeled sulfonyl containing compounds, in particular labeled sulfones and sulfonamides, obtained by a process according to the invention.

Figure 1:
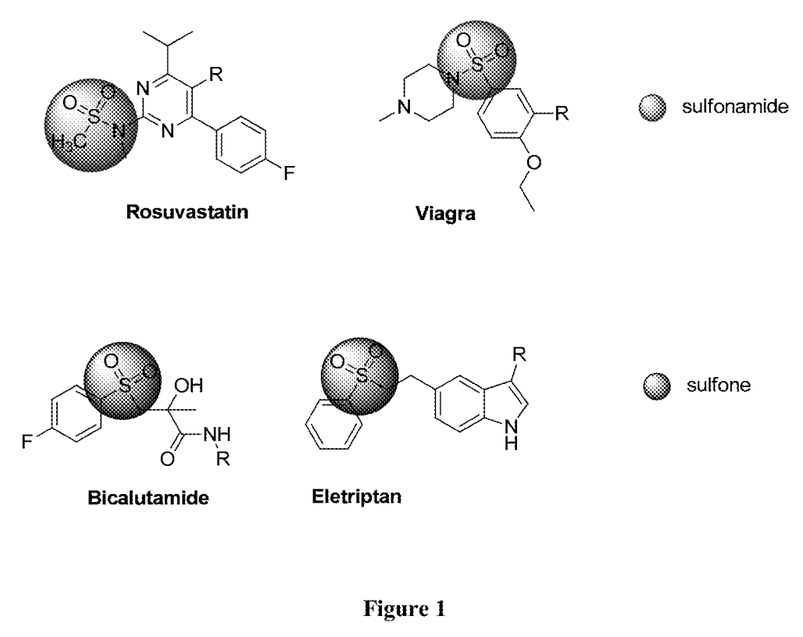
FIG. 1 shows some prominent examples of sulfone and sulfonamide containing drugs.

Both sulfones and sulfonamides represent functional groups with unique characteristics, i.e. stability, lipophilicity and H-bonding etc. (*Sulphones and Sulphoxides* (1988); Patai S., Rappoport Z., Stirling C., Eds.; John Wiley & Sons, Ltd: Chichester, UK, 1988) and are therefore found in a variety of compounds ranging from agrochemicals to pharmaceutical products. Some prominent examples of chemicals bearing these functional groups are bicalutamide for the treatment of prostate cancer, eletriptan against migraine (both sulfone-containing drugs), and Viagra (erectile dysfunction) as well as celebrex, a COX-2 inhibitor (both sulfonamide-containing drugs). From 2014 to 2015, Rosuvastatin, a sulfonamide containing drug, was ranked second based on worldwide sales, highlighting the importance of this class of compounds (FIG. 1). The introduction of sulfone and sulfonamide groups into a molecular skeleton is therefore a key interest of today's organic chemistry.

As the main application of sulfone and sulfonamide containing molecules lies in the area of pharmaceutics and drugs, it is clear that their synthesis is subject to several constraints. Most bioactive compounds bear a variety of functional groups and the introduction of sulfones and/or sulfonamides must therefore tolerate the presence of other structural motifs. Mild reaction conditions, avoiding the use of strong oxidizing or reducing agents or the use of strong acids or bases, is therefore often a prerequisite for the application in synthesis of pharmaceutical products. Further, the use of toxic reactants in the manufacturing process should be reduced to a minimum. Often, the use of metal catalysts is also problematic as strict guidelines exist for the maximum metal content in the final product. Finally, the method for introducing the desired functional group should consist in as few as possible reaction steps with easy purification steps. This implies that the reactants used should be easy to handle, easily synthesized and/or commercially available. In summary, the introduction/formation of sulfones and sulfonamides should proceed under mild conditions in a step-efficient manner using relatively non-toxic and commercially available starting materials.

The classical synthesis of sulfones and sulfonamides generally consists in the oxidation of thiols or thioethers to sulfones or to sulfinate salts. The sulfinate salts can react directly as nucleophiles on C-electrophiles to yield sulfones (Ju Y., Kumar D., Varma, R. S. *J. Org. Chem.* 2006, 71 (17), 6697-6700). Upon chlorination, sulfinate salts can also act as electrophiles and undergo conversion into sulfones or sulfonamides via $S_N2$ substitutions with the corresponding C- or N-nucleophile (Li H.-H., Dong D.-J., Jin Y.-H., Tian S.-K., *J. Org. Chem.* 2009, 74 (24), 9501-9504; Woolven H., González-Rodriguez C., Marco I., Thompson A. L., Willis M. C., *Org. Lett.* 2011, 13 (18), 4876-4878). However, these methods are step-intensive and need oxidizing conditions to generate the sulfones or sulfinate salts. Further, the direct use of sulfinates is limited due to their limited commercial availability and the harsh reaction conditions needed for their synthesis.

Figure 2:
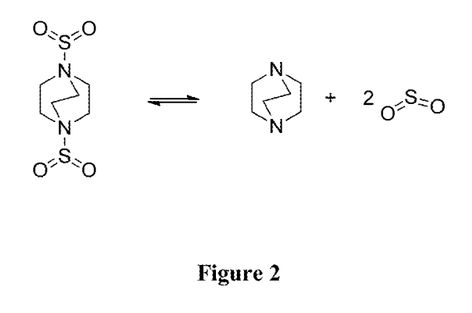
FIG. 2 shows the in situ generation of sulfinates from SO$_2$ or a SO$_2$ surrogate.
Figure 3:
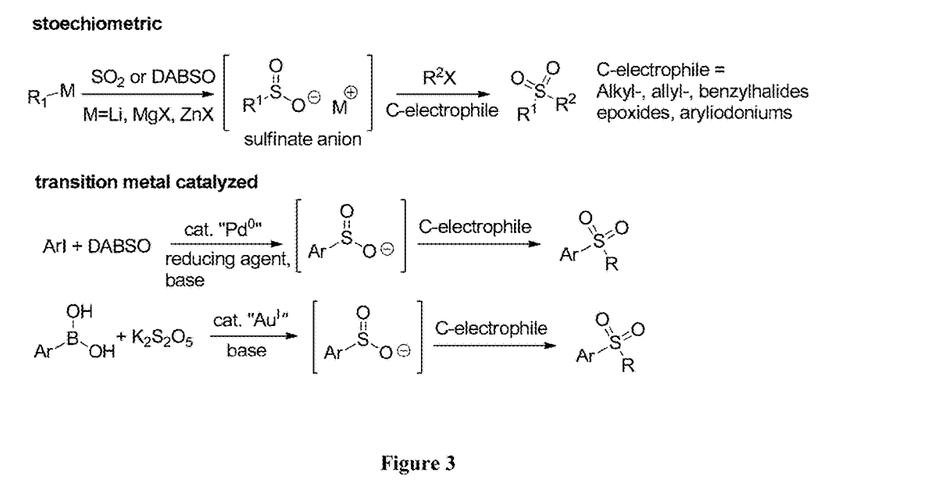
FIG. 3 shows stoichiometric reactions and several transition catalyzed systems for the formation of sulfones.

Therefore, recently, the in situ generation of sulfinates from $SO_2$ or a $SO_2$ surrogate (e.g. 1,4-Diazabicyclo[2.2.2]octane bis(sulfur dioxide) adduct (DABSO)) as shown in FIG. 2 (Woolven H., González-Rodriguez C., Marco I., Thompson A. L., Willis M. C., *Org. Lett.* 2011, 13 (18), 4876-4878), found application in an one-pot procedure to form sulfones or sulfonamides upon trapping the sulfinate with an electrophile (Deeming A. S., Russell C. J., Willis M. C., *Angew. Chem. Int. Ed.* 2015, 54 (4), 1168-1171). Here the sulfinate is generated by addition of an organometallic reagent (i.e. an organolithium, organozinc or organomagnesium) to the $SO_2$ surrogate. In a second step, the so-formed sulfinate salt is trapped by the addition of the electrophile. The use of these organometallic reactants, which are strong nucleophiles and difficult to handle, requires cooling to −40° C., limits the choice of solvents and excludes the direct mixture of all starting materials in an one-pot one-step procedure. The main problem remains thus the in situ sulfinate generation from relatively non-toxic, easy to handle and commercially available starting material under conditions that tolerate the presence of electrophiles. In addition to these stoichiometric reactions, several transition catalyzed systems are also operative for the formation of sulfones (Johnson M. W., Bagley S. W., Mankad N. P., Bergman R. G., Mascitti V., Toste, F. D., *Angew. Chem. Int. Ed.* 2014, 53 (17), 4404-4407; Emmett E. J., Hayter B. R., Willis M. C., Angew. Chem. Int. Ed. 2014, 10204-10208). However, also in these systems, the electrophile has to be added after sulfinate formation in order to prevent the direct quenching of the organometallic species as shown in FIG. 3.

Figure 4:
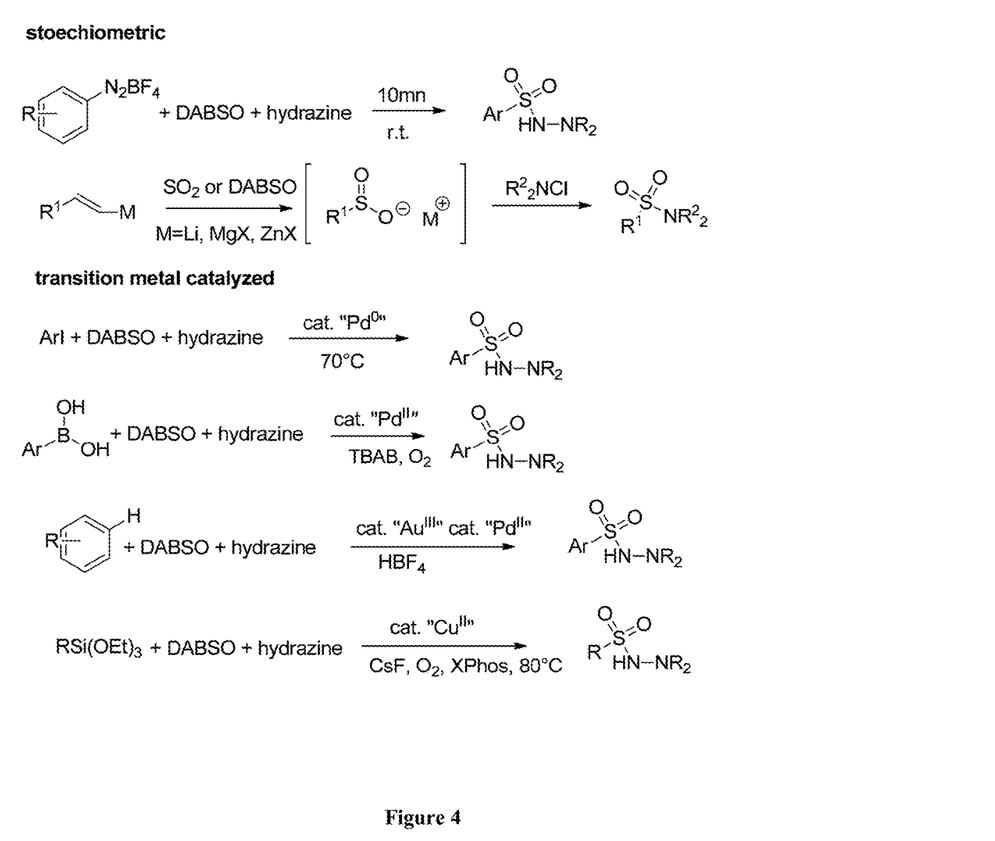
FIG. 4 shows stoichiometric reactions and several transition catalyzed systems for the formation of sulfonamides.

Besides the classical routes mentioned above sulfonamides also can be generated upon addition of an N-electrophile to an in situ generated sulfonate (Deeming A. S., Russell C. J., Willis M. C., *Angew. Chem. Int. Ed.* 2015, 54 (4), 1168-1171). This method consists also in a two-step procedure, where the electrophile is added after sulfinate formation. Further the generation of the electrophilic nitrogen species demands the utilization of oxidizing reagents (i.e. sodium hypochlorite), which might limit the functional group tolerance. A few transition metal catalyzed systems are reported for the formation of sulfonamides from unfunctionalized aryls (Ye S., Wang H., Xiao Q., Ding Q., Wu J., *Adv. Synth. Catal.* 2014, 356 (14-15), 3225-3230), arylhalides (Nguyen B., Emmett E. J., Willis M. C., *J. Am. Chem. Soc.* 2010, 132 (46), 16372-16373), arylboronic esters (Ye S., Wu J., *Chem. Commun.* 2012, 48 (62), 7753-7755) or arylsilanes (Wang X., Xue L., Wang Z., *Org. Lett.* 2014, 16 (15), 4056-4058). The scope of sulfonamides however is limited through the necessity to use hydrazines as N-nucleophiles and no mild one-pot one-step method for the generation of sulfonamides from amines is known so far. All these methods are illustrated in FIG. 4.

Even though the above-described methods are advantageous over the classical routes which employ drastic acidic and oxidizing conditions, the nature of the nucleophiles used (i.e. organometallic species) prevents a successful one-pot one-step procedure. Furthermore, organolithium, organomagnesium, organozinc, or boronicester derivatives are generally laboriously fabricated and rarely commercially available, adding further synthetic steps to the procedure. In order to circumvent this problem, there is a need for a process that is one pot and single step, which implements reactants, in particular, mild nucleophiles whose reaction kinetics allow to distinguish between the different electrophiles present in the reaction medium (i.e. $SO_2$ and the coupling electrophile) thus preventing undesired direct coupling.

Additionally, there is a need for a process that implements reactants that are relatively non-toxic, easy to handle, commercially available and/or can easily be synthesized, and which can be carried out under mild conditions, in particular, under conditions that tolerate the presence of structural groups that may be present in the compounds and reactants involved.

The present invention addresses these needs by providing a process for the synthesis of a compound containing a sulfonyl functional group according to formula (I)

(I)

wherein
R represents $R^1R^2N-$, in which each $R^1$ and $R^2$ is independently an aryl, a heteroaryl, a heterocycle, an alkyl, an alkene, an alkyne or a silyl group, said aryl, heteroaryl, heterocycle, an alkene, an alkyne, silyl and alkyl groups being optionally substituted, or $R^1$ and $R^2$ form together with the nitrogen atom to which they are linked a heterocycle, said heterocycle being optionally substituted; or
R is an aryl, a heteroaryl, a heterocycle, an alkyl, an alkene, an alkyne and a silyl group, said aryl, heteroaryl, heterocycle, an alkene, an alkyne, silyl and alkyl groups being optionally substituted; and
R' is an aryl, a heteroaryl, a heterocycle, an alkyl, an alkene, an alkyne, an amino or a silyl group, said aryl, heteroaryl, heterocycle, an alkene, an alkyne, amino, silyl and alkyl groups being optionally substituted;
said process comprising the step of mixing together
a silane according to formula (II)

$R-Si(X)_3$  (II)

wherein
R is as defined above, and
each X is independently a hydroxyl, —OLi, —ONa, —OK, —OCs, a halogen atom, an alkyl, an alkoxy, an alkene, an aryl, a heteroaryl, a silyl or an amine group;
a $SO_2$ source selected among
$SO_2$ gas,
a $SO_2$ surrogate resulting from heating for 5 minutes or less at a temperature of 600° C. or less a sulfite or a sulfate salt selected among $NaHSO_3$, $Na_2S_2O_5$, $K_2S_2O_5$, $Na_2SO_3$ and $K_2SO_3$, or acidification of a sulfite or a sulfate salt selected among $NaHSO_3$, $Na_2S_2O_5$, $K_2S_2O_5$, $Na_2SO_3$ and $K_2SO_3$ with a an acid having a pKa<3, and
a $SO_2$-amine adduct selected among 1,4-diazabicyclo[2.2.2]octane bis(sulfur dioxide); bis(sulfur dioxide) N,N,N',N'-tetramethylethylenediamine complex and trimethylamine sulfur dioxide;

an electrophilic compound of formula (III)

R'Y  (III)

wherein
R' is as defined above, and
Y is a leaving group selected among
an anionic leaving group selected among a halide, a triflate or trifluoromethylsulfonate, a tosylate or p-toluenesulfonate, a mesylate or methanesulfonate,
a nitrate salt —$ONO_2M$ in which M is a phosphonium selected among arylphosphonium and alkylphosphonium, an ammonium selected among alkyl and arylammoniums, or an alkaline metal selected among Na and K,
a phosphate —$OPO(OH)_2$, a hydrogen phosphate salt —OPO(OH)(OM), or a phosphate salt —$OPO(OM)_2$, in which M is an alkaline metal selected among Na and K, or
R'Y is a diazonium salt $R'-N_2^+Z^-$ in which R' is as defined above and Z is an anionic leaving group as defined above,
R'Y is an oxonium salt $(R')_3O^+L^-$ in which R' is as defined above and L is an anionic non-coordinating ligand, selected among $BF_4^-$, $BPh_4^-$, or $PF_6^-$
R'Y is an acid anhydride R'—C(O)OC(O)R° in which R° is an alkyl, alkenyl, alkynyl, or aryl group and R' as defined above; and
an activating compound selected among
inorganic fluoride salts;
bifluorides;
alkyl and aryl ammonium fluorides;
fluorosilicates;
phosphonium fluorides;
imidazolium fluorides;
a compound comprising two or more fluorine substituents and capable of providing fluoride ions;
an organic fluoride capable of providing fluoride ions;
inorganic salts of alcohols;
inorganic salts of carboxylic;
inorganic or organic salts of carbonates and carbamates; and
optionally a metal catalyst.

The process of the invention is a one pot single step process for synthesis of sulfonyl functional group containing compounds, in particular sulfones and sulfonamides. The different compounds and reactants used in the process of the invention are easy to handle, commercially available and/or can be easily synthesized.

Furthermore, the process of the invention takes place under mild conditions, in particular, under conditions that tolerate the presence of structural groups borne by the compounds and reactants involved in the process of the invention.

The process of the invention is a new process for synthesizing compounds containing a sulfonyl functional group as defined above, in particular, sulfones and sulfonamides.

Figure 5:
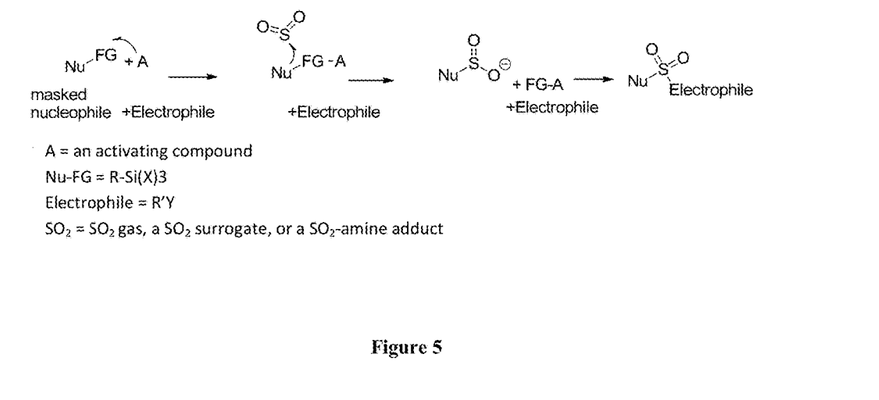
FIG. 5 illustrates the one pot single step process of the invention for synthesizing compounds containing a sulfonyl functional group.

While not wishing to be bound by theory, the choice of the compounds and reactants allows a one pot single step coupling of the nucleophile, the $SO_2$ source, and the electrophile. As mentioned previously, usually direct mixing of an active nucleophile, such as an organometallic species, with $SO_2$ and an electrophile is not possible, due to direct coupling between the active nucleophile and the electrophile without incorporation of $SO_2$. Still not wishing to be bound by theory, in the process of the present invention, the addition of the nucleophile silane of formula (II) and the electrophile of formula (III), to $SO_2$ precedes the addition to the second electrophile. An in situ activation of a mild or non-reactive nucleophile also identified herein as masked nucleophile (i.e. a silane of formula (II)) by an activating compound followed by the reaction of the activated masked nucleophile with SO$_2$ leads to a new stabilized nucleophile, which subsequently interacts with the electrophilic compound of formula (III). The activating compound binds stronger to the masked nucleophile than to the electrophilic compound. This in situ activation thus avoids the direct coupling between the nucleophile (RSi(X)$_3$) and the electrophile (R'Y), and therefore leads to a one-pot, single step procedure. This is illustrated in FIG. 5.

Still not wishing to be bound by theory, in the process of the present invention, when a metal catalyst is used, the metal catalyst is able to activate non-reactive electrophiles, such as aryl or heteroaryl halides.

In a first embodiment, provided herein is a process for the synthesis of a compound containing a sulfonyl functional group according to formula (I)

(I)

wherein
  R represents R$^1$R$^2$N—, in which each R$^1$ and R$^2$ is independently an aryl, a heteroaryl, a heterocycle, an alkyl, an alkene, an alkyne or a silyl group, said aryl, heteroaryl, heterocycle, an alkene, an alkyne, silyl and alkyl groups being optionally substituted, or R$^1$ and R$^2$ form together with the nitrogen atom to which they are linked a heterocycle, said heterocycle being optionally substituted; or
  R is an aryl, a heteroaryl, a heterocycle, an alkyl, an alkene, an alkyne and a silyl group, said aryl, heteroaryl, heterocycle, an alkene, an alkyne, silyl and alkyl groups being optionally substituted; and
  R' is a heterocycle, an alkyl, an alkene, an alkyne, an amino or a silyl group, said aryl, heteroaryl, heterocycle, an alkene, an alkyne, amino, silyl and alkyl groups being optionally substituted;
said process comprising the step of mixing together,
  a silane according to formula (II)

R—Si(X)$_3$  (II)

wherein
  R is as defined above, and
  each X is independently a hydroxyl, —OLi, —ONa, —OK, —OCs, a halogen atom, an alkyl, an alkoxy, an alkene, an aryl, a heteroaryl, a silyl and an amine group;
a SO$_2$ source selected among
  SO$_2$ gas,
  a SO$_2$ surrogate resulting from heating for 5 minutes or less at a temperature of 600° C. or less a sulfite or a sulfate salt selected among NaHSO$_3$, Na$_2$S$_2$O$_5$, K$_2$S$_2$O$_5$, Na$_2$SO$_3$ and K$_2$SO$_3$, or acidification of a sulfite or a sulfate salt selected among NaHSO$_3$, Na$_2$S$_2$O$_5$, K$_2$S$_2$O$_5$, Na$_2$SO$_3$ and K$_2$SO$_3$ with a an acid having a pKa<3, and
  a SO$_2$-amine adduct selected among 1,4-diazabicyclo[2.2.2]octane bis(sulfur dioxide); bis(sulfur dioxide) N,N,N',N'-tetramethylethylenediamine complex and trimethylamine sulfur dioxide;
an electrophilic compound of formula (III)

R'Y  (III)

wherein
  R' is as defined above, and
  Y is a leaving group selected among
    an anionic leaving group selected among a halide, a triflate or trifluoromethylsulfonate, a tosylate or p-toluenesulfonate, a mesylate or methanesulfonate,
    a nitrate salt —ONO$_2$M in which M is a phosphonium selected among arylphosphonium and alkylphosphonium, an ammonium selected among alkyl and arylammoniums, or an alkaline metal selected among Na and K,
    a phosphate —OPO(OH)$_2$, a hydrogen phosphate salt —OPO(OH)(OM), or a phosphate salt —OPO(OM)$_2$, in which M is an alkaline metal selected among Na and K, or
  R'Y is a diazonium salt R'—N$_2$$^+$Z$^-$ in which R' is as defined above and Z is an anionic leaving group as defined above,
  R'Y is an oxonium salt (R')$_3$O$^+$L$^-$ in which R' is as defined above and L is an anionic non-coordinating ligand, selected among BF$_4$$^-$, BPh$_4$$^-$, or PF$_6$$^-$
  R'Y is an acid anhydride R'—C(O)OC(O)R° in which R° is an alkyl, alkenyl, alkynyl, or aryl group and R' as defined above; and
an activating compound selected among
  inorganic fluoride salts;
  bifluorides;
  alkyl and aryl ammonium fluorides;
  fluorosilicates;
  phosphonium fluorides;
  imidazolium fluorides;
  a compound comprising two or more fluorine substituents and capable of providing fluoride ions;
  an organic fluoride capable of providing fluoride ions;
  inorganic salts of alcohols;
  inorganic salts of carboxylic;
  inorganic or organic salts of carbonates and carbamates.

In a second embodiment, provided herein is a process for the synthesis of a compound containing a sulfonyl functional group according to formula (I)

(I)

wherein
  R represents R$^1$R$^2$N—, in which each R$^1$ and R$^2$ is independently an aryl, a heteroaryl, a heterocycle, an alkyl, an alkene, an alkyne or a silyl group, said aryl, heteroaryl, heterocycle, an alkene, an alkyne, silyl and alkyl groups being optionally substituted, or R$^1$ and R$^2$ form together with the nitrogen atom to which they are linked a heterocycle, said heterocycle being optionally substituted; or
  R is an aryl, a heteroaryl, a heterocycle, an alkyl, an alkene, an alkyne and a silyl group, said aryl, heteroaryl, heterocycle, an alkene, an alkyne, silyl and alkyl groups being optionally substituted; and
  R' is an aryl, a heteroaryl, a heterocycle, an alkyl, an alkene, an alkyne, an amino or a silyl group, said aryl, heteroaryl, heterocycle, an alkene, an alkyne, amino, silyl and alkyl groups being optionally substituted;
said process comprising the step of mixing together a silane according to formula (II)

$$R-Si(X)_3 \quad (II)$$

wherein
R is as defined above, and
each X is independently a hydroxyl, —OLi, —ONa, —OK, —OCs, a halogen atom, an alkyl, an alkoxy, an alkene, an aryl, a heteroaryl, a silyl and an amine group;
a $SO_2$ source selected among
$SO_2$ gas,
a $SO_2$ surrogate resulting from heating for 5 minutes or less at a temperature of 600° C. or less a sulfite or a sulfate salt selected among $NaHSO_3$, $Na_2S_2O_5$, $K_2S_2O_5$, $Na_2SO_3$ and $K_2SO_3$, or acidification of a sulfite or a sulfate salt selected among $NaHSO_3$, $Na_2S_2O_5$, $K_2S_2O_5$, $Na_2SO_3$ and $K_2SO_3$ with a an acid having a pKa<3, and
a $SO_2$-amine adduct selected among 1,4-diazabicyclo[2.2.2]octane bis(sulfur dioxide); bis(sulfur dioxide) N,N,N',N'-tetramethylethylenediamine complex and trimethylamine sulfur dioxide;
an electrophilic compound of formula (III)

$$R'Y \quad (III)$$

wherein
R' is as defined above, and
Y is a leaving group selected among
  an anionic leaving group selected among a halide, a triflate or trifluoromethylsulfonate, a tosylate or p-toluenesulfonate, a mesylate or methanesulfonate,
  a nitrate salt —$ONO_2M$ in which M is a phosphonium selected among arylphosphonium and alkylphosphonium, an ammonium selected among alkyl and arylammoniums, or an alkaline metal selected among Na and K,
  a phosphate —$OPO(OH)_2$, a hydrogen phosphate salt —$OPO(OH)(OM)$, or a phosphate salt —$OPO(OM)_2$, in which M is an alkaline metal selected among Na and K, or
R'Y is a diazonium salt R'—$N_2^+Z^-$ in which R' is as defined above and Z is an anionic leaving group as defined above,
R'Y is an oxonium salt $(R')_3O^+L^-$ in which R' is as defined above and L is an anionic non-coordinating ligand, selected among $BF_4^-$, $BPh_4^-$, or $PF_6^-$
R'Y is an acid anhydride R'—C(O)OC(O)R° in which R° is an alkyl, alkenyl, alkynyl, or aryl group and R' as defined above; and
an activating compound selected among
  inorganic fluoride salts;
  bifluorides;
  alkyl and aryl ammonium fluorides;
  fluorosilicates;
  phosphonium fluorides;
  imidazolium fluorides;
  a compound comprising two or more fluorine substituents and capable of providing fluoride ions;
  an organic fluoride capable of providing fluoride ions;
  inorganic salts of alcohols;
  inorganic salts of carboxylic acids;
  inorganic or organic salts of carbonates and carbamates; and
a metal catalyst.

As used herein, a "hydrogen" means $^1H$. Hydrogen may also be radioisotopes of hydrogen (i.e. $^2H$, $^3H$).

As used herein, and unless otherwise indicated, the term "alkyl" means a saturated, monovalent, unbranched, branched or cyclic hydrocarbon groups having $C_1$-$C_{24}$, for example, $C_1$-$C_8$ carbon atoms. Examples of alkyl groups include, but are not limited to, methyl, ethyl, propyl, butyl, pentyl, hexyl, octyl, nonyl, decyl, undecyl, dodecanyl and their branched isomers such as isopropyl, 2-methyl-1-propyl, 2-methyl-2-propyl, 2-methyl-1-butyl, 3-methyl-1-butyl, 2-methyl-3-butyl, 2,2-dimethyl-1 propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, isobutyl, t-butyl, isopentyl, neopentyl. Examples of cyclic alkyl groups include, but are not limited to cyclopropyl, cyclobutyl, cyclopentyl, cyclohexyl, bicylco[2,1,1] hexyl, bicyclo [2,2,1] heptyl, cyclopropylmethyl. An alkyl group can be unsubstituted or substituted with one or more suitable substituents selected among halogen atoms such as fluorine, chlorine, bromine, iodine, hydroxyl, alkoxy, nitro (—$NO_2$), nitrile (—CN), and aryl groups, with alkoxy and aryl groups defined hereinafter. A non-limiting example of an alkyl substituted by an aryl is a benzyl group (—$CH_2$—$C_6H_5$). The alkyl groups may also be isotopologues of natural abundance alkyl groups by being enriched in radioisotopes of carbon (i.e. $^{11}C$, $^{13}C$, $^{14}C$) and/or hydrogen (i.e. $^2H$, $^3H$). The alkyl substituents may also be enriched in radioisotopes of carbon (i.e. $^{11}C$, $^{13}C$, $^{14}C$) oxygen (i.e. $^{18}O$), hydrogen (i.e. $^2H$, $^3H$), nitrogen (i.e. $^{15}N$, $^{13}N$), fluorine (i.e. $^{18}F$, $^{19}F$), chlorine (i.e. $^{37}Cl$), bromine (i.e. $^{79}Br$, $^{81}Br$), iodine (i.e. $^{123}I$, $^{124}I$, $^{125}I$, $^{126}I$).

As used herein, and unless otherwise indicated, the term "alkene" refers to an alkyl group having $C_2$-$C_{24}$, for example, $C_2$-$C_8$ carbon atoms and one or more carbon-carbon double bonds. Examples of alkene groups include, but are not limited to vinyl, allyl, propenyl, butenyl, pentenyl, hexenyl and their branched isomers. Alkene groups may be cyclic or polycyclic. Examples of cyclic alkenes include, but are not limited to, cyclopentenyl, cyclohexenyl. An alkene group can be unsubstituted or substituted with one or more suitable substituents selected among alkyl, halogen atoms such as fluorine, chlorine, bromine, iodine, hydroxyl, alkoxy, nitro (—$NO_2$), nitrile (—CN), and aryl groups, with alkyl as defined previously and alkoxy and aryl groups as defined hereinafter. The alkene groups may also be isotopologues of natural abundance alkene groups by being enriched in radioisotopes of carbon (i.e. $^{11}C$, $^{13}C$, $^{14}C$) and/or hydrogen (i.e. $^2H$, $^3H$). The alkene substituents may also be enriched in radioisotopes of carbon (i.e. $^{11}C$, $^{13}C$, $^{14}C$), oxygen (i.e. $^{18}O$), hydrogen (i.e. $^2H$, $^3H$), nitrogen (i.e. $^{15}N$, $^{13}N$), fluorine (i.e. $^{18}F$, $^{19}F$), chlorine (i.e. $^{37}Cl$), bromine (i.e. $^{79}Br$, $^{81}Br$), iodine (i.e. $^{123}I$, $^{124}I$, $^{125}I$, $^{126}I$).

As used herein, and unless otherwise indicated, the term "alkyne" refers to an alkyl group having $C_2$-$C_{12}$, for example, $C_2$-$C_8$ carbon atoms and one or more carbon-carbon triple bonds. Examples of alkyne groups include, but are not limited to acetylenyl, propynyl, butynyl, pentynyl, hexynyl and their branched isomers. An alkyne group can be unsubstituted or substituted with one or more suitable substituents selected among halogen atoms such as fluorine, chlorine, bromine, iodine, hydroxyl, alkyl, alkoxy, nitro (—$NO_2$), nitrile (—CN), and aryl groups, with alkyl as defined previously and alkoxy and aryl groups defined hereinafter. The alkyne groups may also be isotopologues of natural abundance alkyne groups by being enriched in radioisotopes of carbon (i.e. $^{11}C$, $^{13}C$, $^{14}C$) and/or hydrogen (i.e. $^2H$, $^3H$). The alkyne substituents may also be enriched in radioisotopes of carbon (i.e. $^{11}C$, $^{13}C$, $^{14}C$), oxygen (i.e. $^{18}O$), hydrogen (i.e. $^2H$, $^3H$), nitrogen (i.e. $^{15}N$, $^{13}N$), fluorine (i.e. $^{18}$F, $^{19}$F), chlorine (i.e. $^{37}$Cl), bromine (i.e. $^{79}$Br, $^{81}$Br), iodine (i.e. $^{123}$I, $^{124}$I $^{125}$I, $^{126}$I).

As used herein, and unless otherwise indicated, the term "alkoxy" means an alkyl group as defined above that is linked to another group via an oxygen atom (i.e. —O-alkyl). The alkoxy groups may also be isotopologues of the natural abundance alkoxy groups by being enriched in radioisotopes of carbon (i.e. $^{11}$C, $^{13}$C, $^{14}$C), oxygen (i.e. $^{18}$O) and/or hydrogen (i.e. $^{2}$H, $^{3}$H) and/or nitrogen (i.e. $^{15}$N, $^{13}$N), fluorine (i.e. $^{18}$F, $^{19}$F), chlorine (i.e. $^{37}$Cl), bromine (i.e. $^{79}$Br, $^{81}$Br), iodine (i.e. $^{123}$I, $^{124}$I, $^{125}$I, $^{126}$I) when the alkyl moiety is substituted as defined previously.

As used herein, and unless otherwise indicated, the term "halogen or halide" employed or in combination with other terms means fluorine, chlorine, bromine, iodine and their radioisotopes $^{18}$F, $^{19}$F, $^{37}$Cl, $^{79}$Br, $^{81}$Br, $^{123}$I, $^{124}$I, $^{125}$I, $^{126}$I.

As used herein, and unless otherwise indicated, the term "aryl" employed alone or in combination with other terms means an aromatic hydrocarbon of up to 14 carbon atoms, which can be a single ring (monocyclic) or multiple rings (bicyclic, up to three rings) fused together or linked covalently. Any suitable ring position of the aryl moiety can be covalently linked to the defined chemical structure. Examples of aryl include but are not limited to phenyl, 1-naphtyl, 2-naphtyl, dihydronaphtyl, tetrahydronaphtyl, biphenyl, anthryl, phenanthryl. An aryl group can be unsubstituted or substituted with one or more suitable substituents selected among halogen atoms such as fluorine, chlorine, bromine, iodine, hydroxyl, alkyl, alkoxy, nitro (—NO$_2$), nitrile (—CN), and aryl groups, with alkyl, alkoxy and aryl groups as defined herein. Non-limiting examples of substituted aryl can be methoxyphenyl, trifluoromethylphenyl. The aryl groups may also be isotopologues of natural abundance aryl groups by being enriched in radioisotopes of carbon (i.e. $^{11}$C, $^{13}$C, $^{14}$C) and/or hydrogen (i.e. $^{2}$H, $^{3}$H). When the aryl group is substituted, the substituents may also be enriched in radioisotopes of carbon (i.e. $^{11}$C, $^{13}$C, $^{14}$C), oxygen (i.e. $^{18}$O), hydrogen (i.e. $^{2}$H, $^{3}$H), nitrogen (i.e. $^{15}$N, $^{13}$N) fluorine (i.e. $^{18}$F, $^{19}$F), chlorine (i.e. $^{37}$Cl), bromine (i.e. $^{79}$Br, $^{81}$Br), iodine (i.e. $^{123}$I, $^{124}$I, $^{125}$I, $^{126}$I).

As used herein, and unless otherwise indicated, the term "heteroaryl" means a 5 to 24, for example 5 to 10, membered mono- or polycyclic aromatic substituent where at least 2 atoms are carbon atoms and 1 to 4 atoms are heteroatoms independently selected among nitrogen, oxygen or sulfur. Non limiting examples of heteroaryl groups include furyl, benzofuranyl, pyrrolyl, indolyl, isoindolyl, azaindolyl, thiophenyl, benzothiophenyl, 2-pyridyl, 3-pyridyl, 4-pyridyl, 2-quinolinyl, isoquinolyl, imidazolyl, benzimidazolyl, indolizinyl, pyrazolyl, oxazolyl, isoxazolyl, benzoxazolyl, thiazolyl, benzothiazolyl, isothiazolyl, pyridazinyl, pyrimidinyl, pyrazinyl, triazinyl, cinnolinyl, phtalazinyl, quinazolinyl. The heteroaryl group can be substituted by one or more alkoxy groups; one or more aryl groups; one or more halogen atoms; one or more nitro groups; one or more nitrile groups; one or more alkyl groups, where alkyl, alkoxy and aryl groups are defined as in the present invention. An example of aryl substituted heteroaryl can be phenyloxazolyl. The heteroaryl groups may also be isotopologues of natural abundance heteroaryl groups by being enriched in radioisotopes of carbon (i.e. $^{11}$C, $^{13}$C, $^{14}$C), sulfur (i.e. $^{33}$S, $^{34}$S, $^{35}$S, $^{36}$S), oxygen (i.e. $^{18}$O), nitrogen (i.e. $^{15}$N) and/or hydrogen (i.e. $^{2}$H, $^{3}$H). When the heteroaryl group is substituted, the substituents may also be enriched in radioisotopes of carbon (i.e. $^{11}$C, $^{13}$C, $^{14}$C) oxygen (i.e. $^{18}$O) hydrogen (i.e. $^{2}$H, $^{3}$H), nitrogen (i.e. $^{15}$N, $^{13}$N) fluorine (i.e. $^{18}$F, $^{19}$F), chlorine (i.e. $^{37}$Cl), bromine (i.e. $^{79}$Br, $^{81}$Br) iodine (i.e. $^{123}$I, $^{124}$I, $^{125}$I, $^{126}$I).

As used herein, and unless otherwise indicated, the term "heterocycle" means a 5 to 24, for example, 5 to 10 membered, mono- or polycyclic substituent, saturated or unsaturated (nonaromatic), having 1 to 4 heteroatoms, independently selected among nitrogen oxygen and sulfur. Non limiting examples of heterocycle groups include the morpholinyl, piperidinyle, piperazinyl, pyrrolidinyl, imidazolidinyl, imidazolinyl, pyrazolidinyl, tetrahydrofuranyl, tetrahydropyranyl, thianyl, oxazolidinyl, isoxazolidinyl, thiazolidinyl and isothiazolidinyl substituents. Also included in the definition of heterocycle are moieties that have one or more (i.e. two) aromatic rings fused (i.e. having a bond in common with) to the nonaromatic heterocycle ring, for example, phtalimidyl, indolinyl. The heterocycle can optionally be substituted by one or more hydroxyl groups; one or more alkoxy groups; one or more halogen atoms; one or more nitro groups; one or more nitrile groups; one or more aryl groups; one or more alkyl groups, where alkyl and alkoxy and aryl groups are as defined herein. The heterocycle groups may also be isotopologues of natural abundance heterocycle groups by being enriched in radioisotopes of carbon (i.e. $^{11}$C, $^{13}$C, $^{14}$C), sulfur (i.e. $^{33}$S, $^{34}$S, $^{35}$S, $^{36}$S), oxygen (i.e. $^{18}$O), nitrogen (i.e. $^{15}$N) and/or hydrogen (i.e. $^{2}$H, $^{3}$H). When the heteroaryl group is substituted, the substituents may also be enriched in radioisotopes of carbon (i.e. $^{11}$C, $^{13}$C, $^{14}$C), oxygen (i.e. $^{18}$O), hydrogen (i.e. $^{2}$H, $^{3}$H), nitrogen (i.e. $^{13}$N, $^{15}$N), fluorine (i.e. $^{18}$F, $^{19}$F), chlorine (i.e. $^{37}$Cl), bromine (i.e. $^{79}$Br, $^{81}$Br), iodine (i.e. $^{123}$I, $^{124}$I, $^{125}$I, $^{126}$I).

As used herein and unless otherwise indicated, an alkaline cation means cations of lithium (Li$^+$), sodium (Na$^+$), potassium (K$^+$), rubidium (Rb$^+$), or cesium (Cs$^+$).

A used herein, and unless otherwise indicated, a "silyl" group means a group of formula [—Si(X)$_3$], where X is selected among a hydrogen atom, one or more halogen atoms, one or more alkyl groups, one or more alkoxy groups, one or more aryl groups, with hydrogen, halogen, alkyl, alkoxy and aryl groups defined as in the present invention. The silyl group may also be enriched in radioisotopes of silicium (i.e. $^{29}$Si, $^{30}$Si). Prominent examples comprise the trimethylsilyl, triphenylsilyl, trichlorosilyl, trifluorosilyl, dimethylphenylsilyl, methylphenylsilyl, and the diisopropylterbutylsilyl group.

As used herein, and unless otherwise indicated, a siloxy group corresponds to a silyl group, as defined above that is linked to another group via an oxygen atom (—O—Si(X)$_3$), such as trimethoxy, or triethoxy groups.

As used herein, and unless otherwise indicated, "amine or amino" means a group of formula —NR$^3$R$^4$, where R$^3$ and R$^4$ represents independently, a hydrogen atom, an alkyl group, an alkene group, an alkyne group, an aryl group, an heteroaryl group, a heterocycle, a silyl group, a siloxy group, with hydrogen, alkyl, alkene, alkyne, aryl, heteroaryl, heterocycle, silyl and siloxy as defined as in the present invention, or R$^3$ and R$^4$ taken together with the nitrogen atom to which they are linked from a heterocycle optionally substituted by one or more hydroxyl groups; one or more alkyl groups; one or more alkoxy groups; one or more halogen atoms; one or more nitro groups; one or more nitrile groups; one or more aryl groups; with alkyl, alkoxy and aryl as defined in the present invention.

As used herein, and unless otherwise indicated, the isotopologue of a chemical species has at least one atom with a different number of neutrons than the parent and a radioisotope is radioactive isotope of a chemical element.

As used herein, and unless otherwise indicated, a leaving group means an atom or a molecular fragment that departs with a pair of electrons in heterolytic bond cleavage during a chemical reaction, particularly a nucleophilic displacement reaction Leaving groups can be anions or neutral molecules, but in either case it is crucial that the leaving group be able to stabilize the additional electron density that results from bond heterolysis. Common anionic leaving groups are halides such as Cl$^-$, Br$^-$, and I$^-$, and sulfonate esters such as tosylate (TsO$^-$), mesylate or triflate.

As used herein, and unless otherwise indicated, "activating compound" is a compound that is capable of converting an inactive molecule or a molecule with low activity (i.e. silane of formula (II)) into active molecules that can efficiently undergo a specific chemical reaction.

As indicated, the substituents and the above-defined groups may include, deuterium ($^2$H), du tritium ($^3$H), $^{11}$C, $^{13}$C, $^{14}$C, $^{13}$N, $^{15}$N, $^{18}$O, $^{18}$F, $^{19}$F, $^{29}$Si, $^{30}$Si, $^{33}$S, $^{34}$S, $^{36}$S, $^{36}$S, $^{37}$Cl, $^{79}$Br, $^{81}$Br, $^{123}$I, $^{124}$I, $^{125}$I, $^{126}$I Thus, the process of the invention permits the synthesis of both labeled and unlabeled sulfonyl compounds of formula (I).

In particular, the process of the invention permits a one pot single step synthesis of labeled and unlabeled sulfones and sulfonamides.

A further advantage of the process of the invention is that it uses precise amounts of SO$_2$ source. This is of particular importance for the synthesis of labeled sulfonyl compounds of formula (I).

In an embodiment of the first embodiment of the invention,
  R represents R$^1$R$^2$N—, in which each R$^1$ and R$^2$ is independently an aryl, a heteroaryl, a heterocycle, an alkyl, said aryl, heteroaryl, heterocycle and alkyl groups being optionally substituted, or
  R$^1$ and R$^2$ form together with the nitrogen atom to which they are linked a heterocycle, said heterocycle being optionally substituted; and
  R' is a heterocycle, an alkyl, an alkene, said heterocycle, alkyl and alkene groups being optionally substituted.

In a preferred embodiment of the first embodiment,
  R represents R$^1$R$^2$N—, in which each R$^1$ and R$^2$ is independently methyl, ethyl, propyl, butyl, pentyl, phenyl, tolyl, naphtyl, benzyl group (considered as an alkyl, i.e. methyl, substituted by an aryl, i.e. phenyl group), or
  R$^1$ and R$^2$ form together with the nitrogen atom to which they are linked morpholine, piperidine, oxazoline groups; and
  R' is methyl, ethyl, propyl, butyl, pentyl, allyl, vinyl, or benzyl group.

In an embodiment of the first embodiment of the invention,
  R is an aryl, a heteroaryl, a heterocycle, said aryl, heteroaryl, and heterocycle groups being optionally substituted; and
  R' is a heterocycle, an alkyl, an alkene, said heterocycle, alkene and alkyl groups being optionally substituted.

In a preferred embodiment of the first embodiment of the invention,
  R is 2-pyridyl, 3-pyridyl, 4-pyridyl, 2-thiophenyl, oxazolyl, phenyloxazolyl, methoxyphenyl, trifluoromethylphenyl, allyl or vinyl group; and R' is methyl, ethyl, isopropyl, vinyl, allyl, hexyl, benzyl (considered as an alkyl, i.e. methyl, substituted by an aryl, i.e. phenyl group), morpholinyl.

In an embodiment of the second embodiment of the invention,
  R represents R$^1$R$^2$N—, in which each R$^1$ and R$^2$ is independently an aryl, a heteroaryl, a heterocycle, an alkyl, an alkene group, said aryl, heteroaryl, heterocycle, alkene, and alkyl groups being optionally substituted or
  R$^1$ and R$^2$ form together with the nitrogen atom to which they are linked a heterocycle, said heterocycle being optionally substituted; and
  R' is an aryl, a heteroaryl, a heterocycle, an alkyl, an alkene group, said aryl, heteroaryl, heterocycle, alkene and alkyl groups being optionally substituted.

In a preferred embodiment of the second embodiment of the invention,
  R represents R$^1$R$^2$N—, in which each R$^1$ and R$^2$ is independently methyl, ethyl, propyl, butyl, pentyl, phenyl, tolyl, naphtyl, benzyl group (considered as an alkyl, i.e. methyl, substituted by an aryl, i.e. phenyl group), or
  R$^1$ and R$^2$ form together with the nitrogen atom to which they are linked morpholine, piperidine, oxazoline groups; and
  R' is methyl, ethyl, propyl, butyl, pentyl, allyl, vinyl, benzyl, phenyl, methoxyphenyl, trifluoromethylphenyl, nitrophenyl, cyanophenyl, fluorophenyl, or chlorophenyl group.

In an embodiment of the second embodiment of the invention,
  R is an aryl, a heteroaryl, a heterocycle, an alkene group, said aryl, heteroaryl, heterocycle and alkene groups being optionally substituted; and
  R' is an aryl, a heteroaryl, a heterocycle, an alkyl, an alkene group, said aryl, heteroaryl, heterocycle, alkene and alkyl groups being optionally substituted.

In a preferred embodiment of the second embodiment of the invention,
  R is 2-pyridyl, 3-pyridyl 4-pyridyl, 2-thiophenyl, oxazolyl, phenyloxazolyl, methoxyphenyl, trifluoromethylphenyl, allyl or vinyl group; and
  R' is methyl, ethyl, propyl, butyl, pentyl, allyl, vinyl, benzyl, phenyl, methoxyphenyl, trifluoromethylphenyl, nitrophenyl, cyanophenyl, fluorphenyl, or chlorophenyl group.

The metal catalyst used in the second embodiment of the invention can be an organic or inorganic metal salt or metal complex containing a metal selected among
  metalloids of group 13-16 selected among boron, silicon, aluminum, gallium, tin, indium;
  alkaline metals selected among sodium, potassium;
  alkaline earth metals selected among magnesium, calcium;
  transition metals selected among nickel, iron, cobalt, zinc, copper, rhodium, ruthenium, platinum, palladium, iridium;
  rare earth metals selected among lanthanum, cerium, praseodymium, neodymium.

As used herein, a metal complex is an organometallic or inorganic coordination compound, where the metal ion is linked to an organic or inorganic ligand. An organometallic or inorganic complex might be obtained by mixing a metal salt with a ligand, the latter linking to the metal via phosphorous, sulfur, carbon, nitrogen, silicon, oxygen or hydrogen, for example.

The ligands able to link to the metal salt can be chosen from the following species:

nitrogen bases, as for example, secondary or tertiary amines chosen among triazabicyclodecene (TBD), N-méthyltriazabicyclodecene (MeTBD), 11,8-diazabicyclo[5.4.0]undéc-7-ène (DBU), trimethylamine, triethylemaine, piperidine, 4-diméthylaminopyridine (DMAP), 1,4-diazabicyclo[2.2.2]octane (DABCO), proline, phenylalanine, a thiazolium salt, N-diisopropylethylamine (DIPEA or DIEA);

phosphorous bases, as for example, alkyl and aryl phosphines chosen amongst triphenylphosphine, le 2,2'-bis(diphenylphosphino)-1,1'-binaphthyl (BINAP), triisopropylphosphine, 4,5-Bis(diphenylphosphino)-9,9-dimethylxanthene, 2-Dicyclohexylphosphino-2',4',6'-triisopropylbiphenyl, tricyclohexylphosphine, or di(1-adamantyl)cyclohexylphosphine; alkyl and aryl phosphonates chosen amongst diphenylphosphate, triphenylphosphate (TPP), tri(isopropylphenyl)phosphate (TIPP), cresyldiphenyl phosphate (CDP), le tricresylphosphate (TCP); alkyl and aryl phosphates chosen amongst di-n-butylphosphate (DBP), tris-(2-ethylhexyl)-phosphate, triethyl phosphate;

carbon bases for which protonation occurs on a carbon atom, as for example N-heterocyclic carbenes, carbenes from imidazolium salts such as the salts of 1,3-bis(2,6-diisopropylphenyl)-1H-imidazol-3-ium, 1,3-bis(2,6-diisopropylphenyl)-4,5-dihydro-1H-imidazol-3-ium, 1,3-bis(2,4,6-triméthylphenyl)-1H-imidazol-3-ium, 1,3-bis(2,4,6-triméthylphenyl)-4,5-dihydro-1H-imidazol-3-ium, 4,5-dichloro-1,3-bis(2,6-diisopropylphenyl)-1H-imidazol-3-ium, 1,3-di-tert-butyl-1H-imidazol-3-ium, 1,3-di-tert-butyl-4,5-dihydro-1H-imidazol-3-ium, the present salts being, for example, in the form of their chlorides.

It is of note that the metal catalyst used may be commercially available or generated in situ by the conventional methods known to the skilled person in the art.

In an embodiment of the second embodiment of the invention, the metal may be selected among transition metals as defined hereinabove, preferably, platinum, palladium and copper.

In an embodiment of the second embodiment of the invention the ligand may be selected among phosphorous bases as defined hereinabove, preferably, alkyl and aryl phosphines.

In a preferred embodiment of the second embodiment of the invention, the metal catalyst used can be selected among one of the following precursors: palladium(II) acetate, palladium(II) acetylacetonate, palladium(0) bis(dibenzylidenacetone), palladium (0) tetrakis(triphenylphosphine), allylpalladium(II) chloride dimer, [1,1'-bis(diphenylphosphino)ferrocene]palladium(II) dichloride, optionally in the presence of one of the following ligands: 9,9-dimethyl-4,5-bis(di-tert-butylphosphino)xanthene (tBu-Xantphos), P,P'-(9,9-Dimethyl-9H-xanthene-4,5-diyl)bis[N,N,N',N'-tetraethyl-phosphonous diamide], 4,6-Bis(diphenylphosphino)-10H-phenoxazine, 4,6-Bis(diphenylphosphino)phenoxazine (N-Xantphos), 4,5-Bis(diphenylphosphino)-9,9-dimethylxanthene (Xantphos), 2-Di[3,5-bis(trifluoromethyl)phenylphosphino]-3,6-dimethoxy-2',4',6'-tri-i-propyl-1,1'-biphenyl (JackiePhos) and butyldi-1-adamantylphosphine.

In an embodiment, the process of the invention provides a silane of formula (II) wherein R is as defined in one the above embodiments, and each X is independently a halogen atom, for example, fluorine, chlorine;
an alkoxy, for example methoxy, ethoxy;
an alkyl, for example methyl, ethyl, isopropyl, tertbutyl;
an alkene, for example vinyl, allyl;
an aryl, for example phenyl; and/or
a hydroxyl (—OH), —OLi, —ONa, —OK, —OCs.

The negatively charged oxygen, in the form of its lithium, sodium, potassium or cesium salt can be obtained by the deprotonation of a hydroxy group in situ by an organic or inorganic base, such as DABCO, triethylamine, KH, NaH, LiH, $K_2CO_3$ or other bases with $pK_B<5$. This is well known to the skilled person in the art.

In a preferred embodiment, the process of the invention provides silanes of formula (II) wherein R is 2-pyridyl, 3-pyridyl, 4-pyridyl, 2-thiophenyl, oxazolyl, phenyloxazolyl, methoxyphenyl, trifluoromethylphenyl, allyl or vinyl group, and $—Si(X)_3$ is trichloro-, trifluoro-, trimethoxy-, or dimethylvinyl-silane.

The silane of formula (II) may also be used as a solvent alone or in combination with other solvent(s).

In an embodiment, the process of the invention provides a $SO_2$ source selected among $SO_2$ gas,
a $SO_2$ surrogate resulting from heating at a temperature of 600° C. or less for 5 minutes or less of a sulfite or a sulfate salt selected among $NaHSO_3$, $Na_2S_2O_5$, $K_2S_2O_5$, $Na_2SO_3$ and $K_2SO_3$, or acidification of a sulfite or a sulfate salt selected among $NaHSO_3$, $Na_2S_2O_5$, $K_2S_2O_5$, $Na_2SO_3$ and $K_2SO_3$ with a an acid having a pKa<3, and
a $SO_2$-amine adduct selected among 1,4-diazabicyclo[2.2.2]octane bis(sulfur dioxide) or DABSO; bis(sulfur dioxide) N,N,N',N'-tetramethylethylenediamine complex and trimethylamine sulfur dioxide, in particular DABSO.

In an embodiment, the $SO_2$ source is a $SO_2$-amine adduct as defined hereinabove, in particular, DABSO. In this embodiment, the molar ratio of the $SO_2$-amine adduct, in particular, the molar ratio of DABSO, and silane (II) is between 0.25 to 50, in particular, between 0.5 and 5.

In an embodiment the source of $SO_2$ is a gas. In this embodiment, the $SO_2$ pressure in the reaction vessel is between 0.5 to 100 bar (50 kPa to 10 MPa), in particular between 1 and 30 bar.

In an embodiment, the $SO_2$ source is a $SO_2$ surrogate resulting from the acidification of a sulfite or a sulfate selected among $NaHSO_3$, $Na_2S_2O_5$, $K_2S_2O_5$, $Na_2SO_3$ and $K_2SO_3$ with a an acid selected among HCl, $HSO_4$, $HNO_3$. The molar ratio of sulfite or sulfate and silane (II) used in the acidification reaction is between 0.25 and 50, in particular, between 0.5 and 5. The amount of acid added is in general in excess, in particular, between 5 and 100 mole protons/mole sulfur-atoms.

In an embodiment, the $SO_2$ source is a $SO_2$ surrogate resulting from heating at a temperature of 600° C. or less, in particular 600° C., for 5 minutes or less, in particular 5 minutes, of a sulfite or a sulfate selected among $NaHSO_3$, $Na_2S_2O_5$, $K_2S_2O_5$, $Na_2SO_3$ and $K_2SO_3$. In this embodiment the molar ratio of sulfite or sulfate and silane (II) is between 0.25 and 50, in particular, between 0.5 and 5.

In an embodiment, the process of the invention provides an electrophilic compound of formula (III), wherein R' is as defined above, and Y is a leaving group selected among an anionic leaving group selected among Cl⁻, Br⁻, I⁻, triflate or trifluoromethylsulfonate ($CF_3SO_3^-$), tosylate or p-toluenesulfonate ($CH_3C_6H_4SO_3^-$), mesylate or methanesulfonate ($CH_3SO_3^-$),
a nitrate salt —$ONO_2M$ in which M is a phosphonium selected among arylphosphonium and alkylphosphonium, such as tetrabutyl or tetraphenyl phosponium, or tetrabutyl phosphonium; an ammonium selected among alkyl and arylammoniums, such as tetramethyl-, tetraethyl-, tetrabutyl-, tetraphenyl-ammonium; or an alkaline metal selected among Na and K, a phosphate —OPO(OH)$_2$, a hydrogen phosphate salt —OPO(OH)(OM), and a phosphate salt —OPO(OM)$_2$, in which M is an alkaline metal selected among Na and K, or R'Y is a diazonium salt R'—N$_2^+$Z$^-$ in which R' is as defined above and Z is an anionic leaving group as defined above, R'Y is an oxonium salt (R')$_3$O$^+$L$^-$ in which R' is as defined above and L is an anionic non-coordinating ligand, selected among BF$_4^-$, BPh$_4^-$, or PF$_6^-$, R'Y is an acid anhydride selected among acetic acid anhydride, maleic acid anhydride.

In an embodiment, the process of the invention provides an electrophilic compound of formula (III), wherein R' is as defined above, and Y is an anionic leaving group selected among Cl$^-$, Br$^-$, I$^-$, triflate or trifluoromethylsulfonate (CF$_3$SO$_3^-$), tosylate or p-toluenesulfonate (CH$_3$C$_6$H$_4$SO$_3^-$), mesylate or methanesulfonate (CH$_3$SO$_3^-$).

In an embodiment, the process of the invention provides an electrophilic compound of formula (III), wherein the diazonium salt may be selected among phenyl diazonium chloride, trifluoromethyphenyl dizonium chloride, ethyl diazonium chloride, propyl diazonium chloride.

In an embodiment, the process of the invention provides an electrophilic compound of formula (III), wherein the oxonium salt may be selected among methyl oxonium tetrafluoroborate, ethyl oxonium tetrafluoroborate, propyl oxonium tetrafluoroborate.

The electrophilic compound of formula (III) may also be used as a solvent alone or in combination with other solvent(s).

In all of the embodiments of the invention, the molar ratio between silane (II) and the electrophilic compounds is between 0.1 to 10, in particular between 1 to 3.

In an embodiment, the process of the invention provides inorganic salts of alcohols as activating compounds. In this embodiment, inorganic salts of alcohols are selected among Na or K salts of butyl alcohol, tert-butyl alcohol, iso-propyl alcohol, methyl alcohol and ethyl alcohol.

In an embodiment, the process of the invention provides inorganic salts of carboxylic acids as activating compounds. In this embodiment, the inorganic salts of carboxylic acids are selected among Na or K salts of formic and acetic acid.

In an embodiment, the process of the invention provides inorganic or organic salts of carbonates and carbamates as activating compounds. In this embodiment, the inorganic or organic salts of carbonates and carbamates are selected among Na$_2$CO$_3$, K$_2$CO$_3$, Cs$_2$CO$_3$, CaCO$_3$, MgCO$_3$, lithium methylcarbonate, ammonium salts of dimethylamine carbamate.

In an embodiment, the process of the invention provides inorganic fluoride salts as activating compounds. In this embodiment, the inorganic fluoride salts are selected among NaF, KF, CsF, AlF$_3$, (NH$_4$)$_3$AlF$_6$, CaF$_2$.

In an embodiment, the process of the invention provides bifluorides as activating compounds. In this embodiment, bifluorides are selected among NaHF$_2$, KHF$_2$ and NH$_4$HF$_2$.

In an embodiment, the process of the invention provides an organic source of fluorides as activating compounds. In this embodiment, the organic source of fluorides are selected among:

alkyl and aryl ammonium fluorides, such as tetrabutyl ammonium fluoride (TBAF), tetramethylammonium fluoride, tetrabutylammonium triphenylsilyl difluoride, N,N,N-Trimethyl-1-adamantylammonium fluoride;

fluorosilicates such as tetrabutyl ammonium triphenyldifluorosilicate (TBAT), (NH$_4$)$_2$SiF$_6$, tris(dimethylamino)sulfonium difluorotrimethylsilicate (TASF);

phosphonium fluorides such as tetraphenylphosphonium hydrogen fluoride;

imidazolium fluorides, such a 1H-Imidazol-1-ium fluoride, [bmim][BF4], [bmim][PF6], [bmim][SbF6], [bmim][OTf] with [bmim] representing 1-butyl-3-methylimidazolium;

a compound comprising two or more fluorine substituents and capable of providing fluoride ions such as [(C$_2$H$_5$)$_4$N] PF6, NaHF$_2$, HPF$_6$, NH$_4$PF$_6$, H$_2$SiF$_6$, (NH$_4$)$_2$SiF$_6$, NH$_4$HF$_2$, NaPF$_6$, AlF$_3$ (anhydrous or hydrate), (NH$_4$)$_3$AlF$_6$, (NH$_4$)$_2$TiF$_6$, (NH$_4$)$_2$ZrF$_6$, (NH$_4$)$_2$GeF$_6$, (NH$_4$)$_2$SnF$_6$;

an organic fluoride capable of providing fluoride ions such as ethanolamine hydrofluoride, 9-octadecenylaminhydrofluoride (Dectafluor), (diethylamino)difluorosulfonium tetrafluoroborate (XtalFlour-E®), bis(2-methoxyethyl)aminosulfur trifluoride (Dexo-Fluor®), difluoro(morpholino)sulfonium tetrafluoroborate (XtalFluor-M®), tetrabutylammonium difluorotriphenylstannate and tris(dimethylamino)sulfonium difluorotrimethylsilicate (TASF).

In an embodiment, is provided an activating compound selected among inorganic fluoride salts are selected among NaF, KF, CsF, AlF$_3$, (NH$_4$)$_3$AlF$_6$, CaF$_2$; bifluorides selected among NaHF$_2$, KHF$_2$ and NH$_4$HF$_2$;

an organic source of fluorides selected among:

alkyl and aryl ammonium fluorides selected among tetrabutyl ammonium fluoride (TBAF), tetramethylammonium fluoride, tetrabutylammonium triphenylsilyl difluoride, N,N,N-Trimethyl-1-adamantylammonium fluoride;

fluorosilicates selected among tetrabutyl ammonium triphenyldifluorosilicate (TBAT), (NH$_4$)$_2$SiF$_6$, tris(dimethylamino)sulfonium difluorotrimethylsilicate (TASF);

phosphonium fluorides selected among tetraphenylphosphonium hydrogen fluoride;

imidazolium fluorides, selected among 1H-Imidazol-1-ium fluoride, [bmim][BF4], [bmim][PF6], [bmim][SbF6], [bmim][OTf] with [bmim] representing 1-butyl-3-methylimidazolium;

a compound comprising two or more fluorine substituents and capable of providing fluoride ions selected among [(C$_2$H$_5$)$_4$N] PF6, NaHF$_2$, HPF$_6$, NH$_4$PF$_6$, H$_2$SiF$_6$, (NH$_4$)$_2$SiF$_6$, NH$_4$HF$_2$, NaPF$_6$, AlF$_3$ (anhydrous or hydrate), (NH$_4$)$_3$AlF$_6$, (NH$_4$)$_2$TiF$_6$, (NH$_4$)$_2$ZrF$_6$, (NH$_4$)$_2$GeF$_6$, (NH$_4$)$_2$SnF$_6$;

an organic fluoride capable of providing fluoride ions selected among ethanolamine hydrofluoride, 9-octadecenylaminhydrofluoride (Dectafluor), (diethylamino)difluorosulfonium tetrafluoroborate (XtalFlour-E®), bis(2-methoxyethyl)aminosulfur trifluoride (Dexo-Fluor®), difluoro(morpholino)sulfonium tetrafluoroborate (XtalFluor-M®), tetrabutylammonium difluorotriphenylstannate and tris(dimethylamino)sulfonium difluorotrimethylsilicate (TASF).

In all of the embodiments of the invention, the molar ratio between silane (II) and the activating compound is between 0.5 and 5, in particular between 0.9 and 2.

The process of the invention disposes of several variables which can be changed independently or together to maximize the reaction outcome: the nature of the silane, the electrophile, the activating compound, the $SO_2$ source, concentration of the reactants involved and temperature. The variations can be combined, meaning that the silane can be changed at the same time as the electrophile or the activating compound or the $SO_2$ source. Pressure, temperature and solvent can also be declined independently of the nature of the silane, the electrophile, the activating compound or the $SO_2$ source.

The reaction temperature can be between 0 and 200° C., preferably between 20 and 100° C.

The reaction time can be between 5 minutes and 72 hours, preferably between 1 and 48 hours, still more preferably between 1 and 24 hours.

The process of the invention can occur in a solvent or a mixture of at least two solvents selected among diethylether, dimethylether, dioxane, N-methyl-pyrolidone (NMP), benzene, ethylacetate, chloroform, acetone, nitromethane, dimethylformamide (DMF), dimethylsulfoxide (DMSO), acetonitrile, tetrahy drofurane (THF), dichloromethane (DCM), or toluene.

The silanes of formula (II) are in general easily synthesized or commercially available. Furthermore, they are relatively unreactive depending on the substituents on the silicon atom and on the aromatic ring when an aromatic present is present.

In the embodiments where a metal catalyst is used, said catalyst is present in an amount of 0.00001 to 0.9 molar equivalents with respect to silane (II), in particular, between 0.001 and 0.5 molar equivalents.

Where necessary, the compound containing a sulfonyl functional group of formula (I) obtained by the process of the invention may be purified. Purification of the desired compound may be achieved by conventional methods such as extraction from the aqueous quench and subsequent column chromatography, or by distillation or recrystallization depending on the nature of the sulfonyl group. The skilled person is able to choose the adapted purification method taking into account the nature of the sulfonyl group.

All of the combinations of the embodiments disclosed are encompassed by the present invention.

In another aspect, the invention concerns the process for the synthesis of a compound containing a sulfonyl functional group incorporating radioisotopes and/or stable isotopes.

Isotopically labeled sulfone and sulfonamide containing compounds, incorporating radioisotopes and/or stable isotopes, represent a special interest in several domains as for example, in life science (elucidation and study of enzymatic mechanism, biosynthetic mechanisms, biochemistry, etc.), in environmental science (waste tracing), chemical research (study and elucidation of reaction mechanism) or further the research and development of new pharmaceutics and therapeutics. Therefore, the development of a process for the synthesis of labeled sulfones and sulfonamides, as defined hereafter, meets an urgent need.

Further it is especially important to have a process, which forms isotopically labeled sulfones and sulfonamides from isotopically labeled reactants, such as $^{35}SO_2$, or other $^{35}S$-sulfates. In this regard, the invention also concerns the process for the synthesis of a labeled compound containing a sulfonyl functional group of formula (I'):

wherein R'*, R*, R$^1$*, R$^2$* are defined as previously and comprise optionally H*, C*, N*, O*, F*, Cl*, Br*, I*, S* as defined hereafter:

H* represents an hydrogen atom ($^1$H), a deuterium atom ($^2$H) or a tritium atom ($^3$H)

C* represents a carbon atom ($^{12}$C), an carbon isotope $^{11}$C, $^{13}$C, or $^{14}$C N* represents a nitrogen atom ($^{14}$N) or an isotope $^{15}$N or $^{13}$N, O* represents an oxygen atom ($^{16}$O) or an isotope $^{18}$O, F* represents fluorine ($^{19}$F) or an isotope $^{18}$F,

Cl* represents chlorine ($^{35}$Cl) or an isotope $^{37}$Cl,

Br* represents bromine ($^{80}$Br), an isotope $^{79}$Br or $^{81}$Br,

I* represents iodine $^{127}$I, an isotope $^{123}$I, $^{124}$I, $^{125}$I or $^{126}$I, S* represents a sulfur atom ($^{32}$S), an isotope $^{33}$S, $^{34}$S, $^{35}$S, or $^{36}$S;

said process comprising the step of mixing together a silane according to formula (II')

wherein R*, R$^1$*, R$^2$* are as defined hereinabove and X is defined as previously;

a S*(O*)$_2$ source as defined previously and S* and O* as defined hereinabove;

an electrophilic compound of formula (III')

wherein R'* is as defined hereinabove and Y is defined as previously;

an activating compound as defined hereinabove; and optionally a metal catalyst as previously defined.

Compounds of formula (I') correspond to sulfone or sulfonamides of the formula I with at least one radiolabeled or isotope labeled atom as specified hereinabove. In this regard, isotopes are two atoms of the same element, which differ in number of neutrons, but which have the same number of protons and electrons. Therefore the chemical properties of isotopes of the same element are almost the same. However slight differences in reaction kinetics can exist, when one atom of a reagent is changed for one of its isotopes. As the nucleus of isotopes does not possess of the same number of neutrons, the mass of atoms changes, which might lead to radioactivity and those isotopes are therefore noted as radioisotopes. In the context of this invention the term isotope can include radioisotopes and vice versa.

Radiolabeling consists of adding an isotope to a molecule or compound, which allows to follow its evolution and/or fixation of the labeled molecules, for example in an organ. The radiotracer(s) is/are the radioactive element(s) in a molecule, which allows to follow the pathway of this substance for example in an organ. The process of the invention can therefore give access to labeled sulfonyl containing compounds of formula (I') incorporating one or more of the above-described isotopes. The use of labeled molecules is detailed in the literature (Pleiss, R. Voges, "Synthesis and Applications of Isotopically Labeled Compounds, Volume 7". Wiley-VCH, 2001; R. Voges, J. R. Heys, T. Moenius, "Preparation of Compounds Labeled with Tritium and Carbon-14". Wiley-VCH: Chippenham (UK), 2009).

The major constraints, which limit the synthesis of labeled molecules is the necessity to have a high yield in labeled product with respect to the isotope source used and due to the half lifetime of important isotopes, to have as few synthetic steps as possible in order to minimize the costs linked to the use of radioisotopes.

The process of the invention fulfils this necessity, as for example, $^{35}$S-labeled sulfonyl containing compounds, can be synthesized in a single step from the above-described silanes and $^{35}$SO$_2$, where the amount of labeled SO$_2$ can be precisely controlled with low SO$_2$ pressure (i.e. 1 to 5 atmospheres), or by addition of exact amounts of the SO$_2$-surrogate, for example, DABSO. Further $^{35}$SO$_2$ can be synthesized in a double-chamber system from inorganic $^{35}$S-sulfate or sulfite sources as defined hereinabove by addition of acid, or by heating for 5 minutes or less at a temperature of 600° C. or less.

All of the embodiments and reaction conditions such as the temperature, the reaction time, the solvent(s), and the amounts of reactants and catalysts used in the process for the synthesis of sulfonyl containing compounds of formula (I') are those described hereinabove for the synthesis of sulfonyl containing compounds of formula (I).

Another aspect of the invention concerns the use of sulfonyl containing compounds of formula (I) and labeled sulfonyl containing compound of formula (I') obtained by a process according to the invention in the manufacture of vitamins, pharmaceuticals, adhesives, acrylic fibers and synthetic leathers, pesticides, and fertilizers, for example.

Another aspect of the invention relates to a process for manufacturing vitamins, pharmaceuticals, adhesives, acrylic fibers, synthetic leathers, pesticides, and fertilizers, for example, comprising a step of synthesis of sulfonyl containing compounds of formula (I) and labeled sulfonyl containing compound of formula (I'). This process may optionally comprise a step of solvent extraction and/or purification.

A still another aspect of the invention concerns further relates to a process for producing tracers and tracers, characterized in that it comprises a step of synthesis of a labeled sulfonyl containing compound of formula (I') by the process according to the invention. This process may optionally comprise a step of solvent extraction and/or purification.

Other features and advantages of the present invention appear from the figures and the following non limiting examples.

EXAMPLES

A possible reaction protocol for the synthesis of sulfones and sulfonamides according to the invention may be as follows:

1. In a glove box under argon-atmosphere (recirculating mBraun LabMaster DP) a heteroaryl or aminosilane (Sigma Aldrich) (1 equivalent) is mixed with half an equivalent of the solid SO$_2$-surrogate DABSO (Sigma Aldrich) (0.5-100 equivalents of SO$_2$), a fluoride source (Sigma Aldrich or Alfa Aesar) (1-3 equivalents) and the electrophile (Sigma Aldrich, Alfa Aesar, Acros organics, Strem) (1-3 equivalents) in dry solvent. The concentration of the silane in solution is approximately 0.3 M (based on the volume of the solvent). The introduction order of the substrates does not have any influence on the outcome of the reaction.
2. The reaction mixture is stirred between 5 minutes and 72 h between 20° C. and 100° C. until complete conversion of the silane.
3. Once complete, the reaction medium is quenched by the addition of water and extracted with ethyl acetate. Organic phases are combined and evaporated under reduced pressure. The crude product is purified by silica flash-column chromatography using a pentane/ethyl acetate gradient as eluting agent.

Besides the use of heteroaryl and arylsilanes for the formation of sulfones, sulfonamides can be generated from aminosilanes as nucleophiles following the same procedure.

Example 1

This above protocol was successfully employed to synthesize the following sulfones and sulfonamides:

| Silane (II) | SO$_2$ source | Activating compound | Electrophile (III) | Solvent | Yield (%) | Compound (I) | Catalyst (Temperature |
|---|---|---|---|---|---|---|---|
|  | DABSO | TBAT |  | DCM | 71 |  | None (20° C.) |
|  | DABSO | TBAT |  | DCM | 99 |  | None (20° C.) |

-continued

| Silane (II) | SO₂ source | Activating compound | Electrophile (III) | Solvent | Yield (%) | Compound (I) | Catalyst (Temperature) |
|---|---|---|---|---|---|---|---|
| 2-(SiMe₃)pyridine | DABSO | TBAT | allyl bromide | DCM | 95 | 2-(allylsulfonyl)pyridine | None (20° C.) |
| 2-(SiMe₃)pyridine | DABSO | TBAT | allyl iodide | DCM | 91 | 2-(allylsulfonyl)pyridine | None (20° C.) |
| 2-(SiMe₃)pyridine | DABSO | TBAT | H₃C–I | DCM | 78 | 2-(methylsulfonyl)pyridine | None (20° C.) |
| 2-(SiMe₃)pyridine | DABSO | TBAT | iPr–I | DCM | 60 | 2-(isopropylsulfonyl)pyridine | None (20° C.) |
| 2-(SiMe₃)pyridine | SO₂ from K₂S₂O₅ | CsF | H₃C–I | DMF | 20 | 2-(methylsulfonyl)pyridine | None (20° C.) |
| allyl-Si(OMe)₃ | SO₂ from K₂S₂O₅ | TBAT | 4-iodoanisole | THF | 70 | 4-methoxyphenyl allyl sulfone | 5% Pd(Acac)₂ + 5% Xantphos (100° C.) |
| allyl-Si(OMe)₃ | SO₂ from K₂S₂O₅ | TBAT | 4-iodotoluene | THF | 72 | 4-methylphenyl allyl sulfone | 5% Pd(Acac)₂ + 5% Xantphos (60° C.) |
| allyl-Si(OMe)₃ | SO₂ from K₂S₂O₅ | TBAT | 4-iodotoluene | THF | 38 | 4-methylphenyl allyl sulfone | 5% Pd(dba)₂ + 5% Xantphos (100° C.) |
| N-(SiMe₃)morpholine | DABSO | TBAT | H₃C–I | DCM | 95 | N-(methylsulfonyl)morpholine | None (20° C.) |
| N-(SiMe₃)morpholine | DABSO | TBAT | benzyl bromide | DCM | 70 | N-(benzylsulfonyl)morpholine | None (20° C.) |

| Silane (II) | SO$_2$ source | Activating compound | Electrophile (III) | Solvent | Yield (%) | Compound (I) | Catalyst (Temperature) |
|---|---|---|---|---|---|---|---|
|  | DABSO | TBAT |  | DMF | 50 |  | None (20° C.) |

The invention claimed is:

1. A process for the synthesis of a compound containing a sulfonyl functional group according to formula (I)

(I)

wherein:
R is $R^1R^2N$—, in which
$R^1$ and $R^2$ form together with the nitrogen atom to which they are linked a heterocycle, said heterocycle being optionally substituted with one or more substituents selected from alkyl, alkoxy and aryl groups; or
R is an aryl, a heteroaryl, a heterocycle, an alkyl or an alkene, the aryl, heteroaryl, heterocycle, alkene and alkyl groups being optionally substituted with one or more substituents selected from alkyl, alkoxy and aryl groups; and
R' is an aryl, a heteroaryl, a heterocycle, an alkyl or an alkene, said aryl, heteroaryl, heterocycle, alkene and alkyl groups being optionally substituted with one or more substituents selected from alkyl, alkoxy and aryl groups;
the process comprising the step of mixing together
(i) a silane according to formula (II)

R—Si(X)$_3$ (II)

wherein:
R is as defined above, and
each X is independently an alkyl, an alkoxy or an aryl group;
(ii) a SO$_2$ source selected from the group consisting of: SO$_2$ gas,
a SO$_2$ surrogate resulting from heating for 5 minutes or less at a temperature of 600° C. or less a sulfite or a sulfate salt selected among NaHSO$_3$, Na$_2$S$_2$O$_5$, K$_2$S$_2$O$_5$, Na$_2$SO$_3$ and K$_2$SO$_3$, or acidification of a sulfite or a sulfate salt selected from the group consisting of: NaHSO$_3$, Na$_2$S$_2$O$_5$, K$_2$S$_2$O$_5$, Na$_2$SO$_3$ and K$_2$SO$_3$ with an acid having a pKa<3, and
a SO$_2$-amine adduct selected from the group consisting of: 1,4-diazabicyclo[2.2.2]octane bis(sulfur dioxide); bis(sulfur dioxide) N,N,N',N'-tetramethylethylenediamine complex and trimethylamine sulfur dioxide;
(iii) an electrophilic compound of formula (III)

R'Y (III)

wherein:
R' is as defined above, and
Y is a leaving group selected from the group consisting of:
an anionic leaving group selected from the group consisting of: a halide, a trifluoromethylsulfonate, a p-toluenesulfonate, and a methanesulfonate; and (iv) an activating compound selected from the group consisting of:
inorganic fluoride salts selected from NaF, KF, CsF, AlF$_3$, (NH$_4$)$_3$AlF$_6$ and CaF$_2$;
an organic fluoride capable of providing fluoride ions selected from alkyl and aryl ammonium fluorides and fluorosilicates; and
optionally a metal catalyst which is an inorganic metal salt or a metal complex containing a metal selected from platinum, palladium and copper and a ligand able to link to the metal salt selected from alkyl and aryl phosphines.

2. The process according to claim 1,
wherein:
R is $R^1R^2N$—, in which
$R^1$ and $R^2$ form together with the nitrogen atom to which they are linked a heterocycle, the heterocycle being optionally substituted with one or more substituents selected from alkyl, alkoxy and aryl groups; or
R is an aryl, a heteroaryl, a heterocycle, an alkyl or an alkene, the aryl, heteroaryl, heterocycle, alkene and alkyl groups being optionally substituted with one or more substituents selected from alkyl, alkoxy and aryl groups; and
R' is an aryl, a heteroaryl, a heterocycle, an alkyl or an alkene, the aryl, heteroaryl, heterocycle, alkene and alkyl groups being optionally substituted with one or more substituents selected from alkyl, alkoxy and aryl groups;
the process comprising the step of mixing together,
(i) a silane according to formula (II)

R—Si(X)$_3$ (II)

wherein:
R is as defined above, and
each X is independently an alkyl, an alkoxy or an aryl group;
(ii) a SO$_2$ source selected from the group consisting of: SO$_2$ gas,
a SO$_2$ surrogate resulting from heating for 5 minutes or less at a temperature of 600° C. or less a sulfite or a sulfate salt selected from the group consisting of: NaHSO$_3$, Na$_2$S$_2$O$_5$, K$_2$S$_2$O$_5$, Na$_2$SO$_3$ and K$_2$SO$_3$, or acidification of a sulfite or a sulfate salt selected from the group consisting of: NaHSO$_3$, Na$_2$S$_2$O$_5$, K$_2$S$_2$O$_5$, Na$_2$SO$_3$ and K$_2$SO$_3$ with an acid having a pKa<3, and
a SO$_2$-amine adduct selected from the group consisting of: 1,4-diazabicyclo[2.2.2]octane bis(sulfur dioxide); bis(sulfur dioxide) N,N,N',N'-tetramethylethylenediamine complex and trimethylamine sulfur dioxide;
(iii) an electrophilic compound of formula (III)

R'Y  (III)

wherein:
R' is as defined above, and
Y is a leaving group selected from the group consisting of:
an anionic leaving group selected from the group consisting of: a halide, a trifluoromethylsulfonate, a p-toluenesulfonate, and a methanesulfonate;
(iv) an activating compound selected from the group consisting of:
inorganic fluoride salts selected from NaF, KF, CsF, $AlF_3$, $(NH_4)_3AlF_6$ and $CaF_2$;
an organic fluoride capable of providing fluoride ions selected from alkyl and aryl ammonium fluorides and fluorosilicates.

3. The process according to claim 1,
wherein:
R represents $R^1R^2N—$, in which
$R^1$ and $R^2$ form together with the nitrogen atom to which they are linked a heterocycle, said heterocycle being optionally substituted with one or more substituents selected from alkyl, alkoxy and aryl groups; or
R is an aryl, a heteroaryl, a heterocycle, an alkyl or an alkene, the aryl, heteroaryl, heterocycle, alkene and alkyl groups being optionally substituted with one or more substituents selected from alkyl, alkoxy and aryl groups; and
R' is an aryl, a heteroaryl, a heterocycle, an alkyl or an alkene, the aryl, heteroaryl, heterocycle, alkene and alkyl groups being optionally substituted with one or more substituents selected from alkyl, alkoxy and aryl groups;
the process comprising the step of mixing together
(i) a silane according to formula (II)

$$R—Si(X)_3 \quad (II)$$

wherein:
R is as defined above, and
each X is independently an alkyl, an alkoxy or an aryl group;
(ii) a $SO_2$ source selected from the group consisting of:
$SO_2$ gas,
a $SO_2$ surrogate resulting from heating for 5 minutes or less at a temperature of 600° C. or less a sulfite or a sulfate salt selected from the group consisting of: $NaHSO_3$, $Na_2S_2O_5$, $K_2S_2O_5$, $Na_2SO_3$ and $K_2SO_3$, or acidification of a sulfite or a sulfate salt selected from the group consisting of: $NaHSO_3$, $Na_2S_2O_5$, $K_2S_2O_5$, $Na_2SO_3$ and $K_2SO_3$ with an acid having a pKa<3, and
a $SO_2$-amine adduct selected from the group consisting of: 1,4-diazabicyclo[2.2.2]octane bis(sulfur dioxide); bis(sulfur dioxide) N,N,N',N'-tetramethylethylenediamine complex and trimethylamine sulfur dioxide;
(iii) an electrophilic compound of formula (III)

$$R'Y \quad (III)$$

wherein:
R' is as defined above, and
Y is a leaving group selected from the group consisting of:
an anionic leaving group selected from the group consisting of: a halide, a trifluoromethylsulfonate, a p-toluenesulfonate, and a methanesulfonate; and
(iv) an activating compound selected from the group consisting of:
inorganic fluoride salts selected from NaF, KF, CsF, $AlF_3$, $(NH_4)_3AlF_6$ and $CaF_2$;
an organic fluoride capable of providing fluoride ions selected from alkyl and aryl ammonium fluorides and fluorosilicates;
a metal catalyst which is an inorganic metal salt or a metal complex containing a metal selected from platinum, palladium and copper and a ligand able to line to the metal salt selected from alkyl and aryl phosphines.

4. The process according to claim 1,
wherein:
R is $R^1R^2N—$, in which
$R^1$ and $R^2$ form together with the nitrogen atom to which they are linked a heterocycle, said heterocycle being optionally substituted with one or more substituents selected from alkyl, alkoxy and aryl groups; and
R' is a heterocycle, an alkyl or an alkene, the heterocycle, alkyl and alkene groups being optionally substituted with one or more substituents selected from alkyl, alkoxy and aryl groups.

5. The process according to claim 1,
wherein:
R is an alkene, an aryl, a heteroaryl or a heterocycle, the alkene, aryl, heteroaryl, and heterocycle groups being optionally substituted with one or more substituents selected from alkyl, alkoxy and aryl groups; and
R' is an aryl, a heterocycle, an alkyl or an alkene, the aryl, heterocycle, alkene and alkyl groups being optionally substituted with one or more substituents selected from alkyl, alkoxy and aryl groups.

6. The process according to claim 1,
wherein:
R is $R^1R^2N—$, in which
$R^1$ and $R^2$ form together with the nitrogen atom to which they are linked a heterocycle, the heterocycle being optionally substituted with one or more substituents selected from alkyl, alkoxy and aryl groups; and
R' is an aryl, a heteroaryl, a heterocycle, an alkyl or an alkene group, the aryl, heteroaryl, heterocycle, alkene and alkyl groups being optionally substituted with one or more substituents selected from alkyl, alkoxy and aryl groups.

7. The process according to claim 1,
wherein:
R is an aryl, a heteroaryl, a heterocycle or an alkene group, the aryl, heteroaryl, heterocycle and alkene groups being optionally substituted with one or more substituents selected from alkyl, alkoxy and aryl groups; and
R' is an aryl, a heteroaryl, a heterocycle, an alkyl or an alkene group, the aryl, heteroaryl, heterocycle, alkene and alkyl groups being optionally substituted with one or more substituents selected from alkyl, alkoxy and aryl groups.

8. The process according to claim 1,
wherein:
the metal catalyst is an inorganic metal salt or metal complex containing a metal selected from the group consisting of:
transition metals selected from the group consisting of: copper, platinum and palladium; and
a ligand able to link to the metal salt selected from the group consisting of:
alkyl and aryl phosphines selected from the group consisting of: triphenylphosphine, 2,2'-bis(diphenylphosphino)-1,1'-binaphthyl (BINAP), triisopropylphosphine, 4,5-bis(diphenylphosphino)-9,9-dimethylxanthene, 2-dicyclohexylphosphino-2',4',6'-triisopropylbiphenyl, tricyclohexylphosphine and di(1-adamantyl)cyclohexylphosphine.

9. The process according to claim 1, wherein the metal catalyst is present in an amount of 0.00001 to 0.9 molar equivalents with respect to silane (II).

10. The process according to claim 1, wherein each X is independently methoxy, ethoxy, methyl, ethyl, isopropyl, tertbutyl or phenyl.

11. The process according to claim 1,
wherein the $SO_2$ source is selected from the group consisting of:
$SO_2$ gas,
a $SO_2$ surrogate resulting from heating at a temperature of 600° C. or less for 5 minutes or less of a sulfite or a sulfate salt selected from the group consisting of: $NaHSO_3$, $Na_2S_2O_5$, $K_2S_2O_5$, $Na_2SO_3$ and $K_2SO_3$, or acidification of a sulfite or a sulfate salt selected from the group consisting of: $NaHSO_3$, $Na_2S_2O_5$, $K_2S_2O_5$, $Na_2SO_3$ and $K_2SO_3$ with an acid having a pKa<3, and
a $SO_2$-amine adduct selected from the group consisting of: 1,4-diazabicyclo[2.2.2]octane bis(sulfur dioxide) or DABSO.

12. The process according to claim 11,
wherein when the $SO_2$ source is selected from the group consisting of:
DABSO, where the molar ratio of DABSO and silane (II) is between 0.25 to 50;
$SO_2$ gas, where the $SO_2$ pressure in the reaction vessel is between 0.5 to 100 bar;
a $SO_2$ surrogate resulting from the acidification of a sulfite or a sulfate selected from the group consisting of: $NaHSO_3$, $Na_2S_2O_5$, $K_2S_2O_5$, $Na_2SO_3$ and $K_2SO_3$ with an acid selected from the group consisting of: HCl, $HSO_4$ and $HNO_3$, where the molar ratio of sulfite or sulfate and silane (II) used in the acidification reaction is between 0.25 and 50, and the amount of acid added is between 5 and 100 mol protons/mol sulfur-atoms;
a $SO_2$ surrogate resulting from heating at a temperature of 600° C. or less for 5 minutes or less of a sulfite or a sulfate selected from the group consisting of: $NaHSO_3$, $Na_2S_2O_5$, $K_2S_2O_5$, $Na_2SO_3$ and $K_2SO_3$, where the molar ratio of sulfite or sulfate and silane (II) is between 0.25 and 50.

13. The process according to claim 1,
wherein Y is a leaving group selected from the group consisting of:
an anionic leaving group selected from the group consisting of: $Cl^-$, $Br^-$, $I^-$, trifluoromethylsulfonate, p-toluenesulfonate and methanesulfonate.

14. The process according to claim 1, wherein the molar ratio between silane (II) and the electrophilic compounds is between 0.1 to 10.

15. The process according to claim 1, wherein the activating compound is selected from the group consisting of:
inorganic fluoride salts are selected from the group consisting of: NaF, KF, CsF, $AlF_3$, $(NH_4)_3AlF_6$ and $CaF_2$;
bifluorides selected from the group consisting of: $NaHF_2$, $KHF_2$ and $NH_4HF_2$;
an organic source of fluorides selected from the group consisting of:
alkyl and aryl ammonium fluorides selected from the group consisting of: tetrabutyl ammonium fluoride (TBAF), tetramethylammonium fluoride, tetrabutylammonium triphenylsilyl difluoride and N,N,N-trimethyl-1-adamantylammonium fluoride;
fluorosilicates selected from the group consisting of: tetrabutyl ammonium triphenyldifluorosilicate (TBAT), $(NH_4)_2SiF_6$ and tris(dimethylamino)sulfonium difluorotrimethylsilicate (TASF).

16. The process according to claim 1, wherein the molar ratio between silane (II) and the activating compound is between 0.5 and 5.

* * * * *